(12) United States Patent
Collier et al.

(10) Patent No.: US 10,730,813 B2
(45) Date of Patent: *Aug. 4, 2020

(54) METHOD FOR PRODUCING AND PURIFYING 2,3,3,3-TETRAFLUOROPROPENE

(71) Applicant: Arkema France, Colombes (FR)

(72) Inventors: Bertrand Collier, Saint-genis-laval (FR); Dominique Deur-Bert, Charly (FR); Joaquin Lacambra, Vernaison (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,031

(22) Filed: Jul. 24, 2019

(65) Prior Publication Data

US 2019/0345083 A1    Nov. 14, 2019

Related U.S. Application Data

(63) Continuation of application No. 16/063,302, filed as application No. PCT/EP2016/080949 on Dec. 14, 2016, now Pat. No. 10,407,369.

(30) Foreign Application Priority Data

Dec. 23, 2015   (FR) ..................... 15 63168

(51) Int. Cl.
   *C07C 17/25*   (2006.01)
   *C07C 17/20*   (2006.01)
   (Continued)

(52) U.S. Cl.
   CPC .......... *C07C 17/383* (2013.01); *C07C 17/206* (2013.01); *C07C 17/25* (2013.01);
   (Continued)

(58) Field of Classification Search
   None
   See application file for complete search history.

(56) References Cited

U.S. PATENT DOCUMENTS

2014/0031597 A1   1/2014   Deur-Bert et al.
2014/0039228 A1   2/2014   Pigamo et al.

FOREIGN PATENT DOCUMENTS

EP   939071 A1   9/1999
EP   0864554 B1   9/2002
(Continued)

OTHER PUBLICATIONS

ISA/EPO ; International Search Report for International Patent Application No. PCT/EP2016/080949 dated Mar. 17, 2017, 10 pages.

*Primary Examiner* — Medhanit W Bahta
(74) *Attorney, Agent, or Firm* — NK Patent Law

(57) ABSTRACT

The invention relates to a process for producing 2,3,3,3-tetrafluoropropene performed using a starting composition, comprising the steps of placing the starting composition in contact with HF, in the presence of a catalyst, to produce a composition A comprising 2,3,3,3-tetrafluoropropene (1234yf), intermediate products B consisting of 2-chloro-3,3,3-trifluoropropene (1233xf), 1,1,1,2,2-pentafluoropropane (245cb), and side products C consisting of E-1-chloro-3,3,3-trifluoro-1-propene (1233zdE), trans-1,3,3,3-tetrafluoro-1-propene (1234zeE) and 1,1,1,3,3-pentafluoropropane (245fa); recovery of said composition A and purification thereof to form and recover a first stream comprising 2,3,3,3-tetrafluoropropene (1234yf) and one or more streams comprising 2-chloro-3,3,3-trifluoropropene (1233xf) and/or 1,1,1,2,2-pentafluoropropane (245cb); recycling into step a) of said one or more streams comprising 2-chloro-3,3,3-trifluoropropene (1233xf) and/or 1,1,1,2,2-pentafluoropropane (245cb).

10 Claims, 3 Drawing Sheets

(51) Int. Cl.
*C07C 21/18* (2006.01)
*C07C 17/38* (2006.01)
*C07C 17/383* (2006.01)
*C07C 19/08* (2006.01)

(52) U.S. Cl.
CPC .............. *C07C 17/38* (2013.01); *C07C 19/08* (2013.01); *C07C 21/18* (2013.01)

(56) References Cited

FOREIGN PATENT DOCUMENTS

| | | |
|---|---|---|
| WO | 1998019982 | 5/1998 |
| WO | 2003068716 A1 | 8/2003 |
| WO | 2007079431 A2 | 7/2007 |
| WO | 2008040969 A2 | 4/2008 |
| WO | 2008054781 A1 | 5/2008 |
| WO | 3013088195 A1 | 6/2013 |

METHOD FOR PRODUCING AND PURIFYING 2,3,3,3-TETRAFLUOROPROPENE

CROSS-REFERENCE TO RELATED APPLICATIONS

This application is a continuation of U.S. patent application Ser. No. 16/063,302 filed on Jun. 18, 2018, which is a U.S. National Stage application of International Patent Application No. PCT/EP2016/080949 filed on Dec. 14, 2016, which claims the benefit of French Patent Application No. 1563168 filed on Dec. 23, 2015.

TECHNICAL FIELD OF THE INVENTION

The invention relates to a process for purifying 2,3,3,3-tetrafluoro-1-propene. In addition, the invention also relates to a process for producing and purifying 2,3,3,3-tetrafluoro-1-propene.

TECHNOLOGICAL BACKGROUND OF THE INVENTION

Hydrofluorocarbons (HFCs) and in particular hydrofluoroolefins (HFOs), such as 2,3,3,3-tetrafluoro-1-propene (HFO-1234yf), are compounds known for their properties as coolants and heat-transfer fluids, extinguishers, propellants, foaming agents, swelling agents, gaseous dielectrics, polymerization medium or monomer, support fluids, agents for abrasives, drying agents and fluids for power production units.

HFOs have been identified as desirable alternatives to HCFC on account of their low ODP (ozone depletion potential) and GWP (global warming potential) values.

Most of the processes for manufacturing hydrofluoroolefins involve a fluorination and/or dehydrohalogenation reaction. This type of reaction is performed in the gas phase and generates impurities which consequently need to be removed in order to obtain the desired compound in a sufficient degree of purity for the targeted applications.

For example, in the context of producing 2,3,3,3-tetrafluoro-1-propene (HFO-1234yf), the presence of impurities such as 1-chloro-3,3,3-trifluoro-1-propene (1233zd), 1,3,3,3-tetrafluoro-1-propene (1234ze) and 1,1,1,3,3-pentafluoropropane (245fa) is observed. These impurities are isomers of the main compounds that are desired to be obtained via the process for producing 2,3,3,3-tetrafluoro-1-propene, besides the latter, i.e. 2-chloro-3,3,3-trifluoro-1-propene (1233xf) and 1,1,1,2,2-pentafluoropropane (245cb). Given the respective boiling points of 1-chloro-3,3,3-trifluoro-1-propene (1233zd), 1,3,3,3-tetrafluoro-1-propene (1234ze) and 1,1,1,3,3-pentafluoropropane (245fa), they may accumulate in the reaction loop and thus prevent the formation of the products of interest.

Purification of this type of reaction mixture may be performed via various techniques known from the prior art, for instance distillation. However, when the compounds to be purified have boiling points that are too close or when they form azeotropic or quasi-azeotropic compositions, distillation is not an efficient process. Extractive distillation processes have thus been described.

EP 0 864 554 discloses a process for purifying a mixture comprising 1,1,1,3,3-pentafluoropropane (245fa) and 1-chloro-3,3,3-trifluoro-trans-1-propene (1233zd) by distillation in the presence of a solvent with a boiling point of greater than that of 1-chloro-3,3,3-trifluoro-trans-1-propene.

WO 03/068716 discloses a process for recovering pentafluoroethane from a mixture comprising pentafluoroethane and chloropentafluoroethane by distillation in the presence of hexafluoropropene.

WO 98/19982 also discloses a process for purifying 1,1-difluoroethane by extractive distillation. The process consists in placing an extracting agent in contact with a mixture of 1,1-difluoroethane and vinyl chloride. The extracting agent is chosen from hydrocarbons, alcohols and chlorocarbons with a boiling point of between 10° C. and 120° C. As mentioned by WO 98/19982, the selection of the extracting agent may prove to be complex depending on the products to be separated. WO 2013/088195 discloses a process for preparing 2,3,3,3-tetrafluoropropene from 1,1,1,2,3-pentachloropropane and/or 1,1,2,2,3-pentachloropropane. There is thus still a need to develop a particular process for purifying 2,3,3,3-tetrafluoro-1-propene.

SUMMARY OF THE INVENTION

In a process for producing 2,3,3,3-tetrafluoro-1-propene, the choice of particular operating conditions makes it possible to promote the presence of certain impurities or of isomers thereof. The presence of impurities such as 1,3,3,3-tetrafluoro-1-propene (1234ze) may be observed, as may that of 1-chloro-3,3,3-trifluoro-1-propene (1233zd) and 1,1,1,3,3-pentafluoropropane (245fa). These impurities may derive from side reactions induced by intermediate compounds produced during the production of 2,3,3,3-tetrafluoro-1-propene, and may have physical properties such that the removal thereof may prove to be complex. The present invention especially allows the production of 2,3,3,3-tetrafluoro-1-propene in improved purity.

According to a first aspect, the invention provides a process for producing and purifying 2,3,3,3-tetrafluoropropene (1234yf) which is performed using a starting composition comprising at least one compound of formula $CX(Y)_2-CX(Y)_m-CH_mXY$ (I) in which X and Y independently represent H, F or Cl and m=0 or 1; and/or fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

said process comprising the steps of:
a) placing the starting composition in contact, in the presence of a catalyst, with HF to produce a composition A comprising HCl, part of the unreacted HF, 2,3,3,3-tetrafluoropropene (1234yf), intermediate products B consisting of 2-chloro-3,3,3-trifluoropropene (1233xf), 1,1,1,2,2-pentafluoropropane (245cb), and side products C consisting of E-1-chloro-3,3,3-trifluoro-1-propene (1233zdE), trans-1,3,3,3-tetrafluoro-1-propene (1234zeE) and 1,1,1,3,3-pentafluoropropane (245fa);
b) recovery of said composition A and purification, preferably distillation, thereof to form and recover a first stream, which is preferably gaseous, comprising HCl, 2,3,3,3-tetrafluoropropene (1234yf), part of the intermediate products B and part of the side products C; and a stream, which is preferably liquid, L comprising part of the unreacted HF, part of the intermediate products B and part of the side products C;
c) purification of said first stream to form a stream comprising part of said intermediate products B and part of the side products C and recycling thereof into step a).

According to a preferred embodiment, said first stream is a gaseous stream G1 which is purified via the following steps:
- b1) distillation of the gaseous stream G1 to recover a stream G1a comprising HCl, advantageously at the top of the distillation column, and a stream G1b comprising 2,3,3,3-tetrafluoropropene (1234yf), said part of the intermediate products B and said part of the side products C, advantageously at the bottom of the distillation column;
- b2) distillation of said stream G1b obtained in step b1) to form a stream G1c comprising 2,3,3,3-tetrafluoropropene (1234yf), a portion of said part of the intermediate products B and a portion of said part of the side products C, advantageously at the top of the distillation column, and a stream G1d comprising a portion of said part of the intermediate products B and a portion of said part of the side products C, advantageously at the bottom of the distillation column; preferably, the stream G1d is recycled into step a).

Preferably, the stream G1c formed in step b2) may comprise 2,3,3,3-tetrafluoropropene (1234yf), 1,1,1,2,2-pentafluoropropane (245cb) and trans-1,3,3,3-tetrafluoro-1-propene (1234zeE). Preferably, the stream G1d formed in step b2) may comprise 1,1,1,2,2-pentafluoropropane (245cb), trans-1,3,3,3-tetrafluoro-1-propene (1234zeE) and 2-chloro-3,3,3-trifluoropropene (1233xf). In particular, the content of 1,1,1,2,2-pentafluoropropane (245cb) is greater in stream G1d than in stream G1c.

According to a preferred embodiment, the process comprises a step b3), subsequent to step b2), in which the stream G1c obtained in step b2) comprises 2,3,3,3-tetrafluoropropene (1234yf), 1,1,1,2,2-pentafluoropropane (245cb) and trans-1,3,3,3-tetrafluoro-1-propene (1234zeE); and said stream G1c is distilled to form a stream G1e comprising 2,3,3,3-tetrafluoropropene (1234yf) and a stream G1f comprising 1,1,1,2,2-pentafluoropropane (245cb) and trans-1,3,3,3-tetrafluoro-1-propene (1234zeE). Preferably, the stream G1e comprising 2,3,3,3-tetrafluoropropene (1234yf) may be subjected to subsequent purification steps so as to obtain a degree of purity sufficient for its marketing.

According to a preferred embodiment, the stream G1f obtained in step b3) is separated out by extractive distillation.

According to a particular embodiment, the stream G1f obtained in step b3) is separated out by extractive distillation according to the following steps:
- b4) placing said stream G1f obtained in step b3) in contact with an organic extracting agent to form a stream G1g, and
- b5) extractive distillation of the stream G1g to form a stream G1h comprising 1,1,1,2,2-pentafluoropropane (245cb), advantageously at the top of the distillation column, and a stream G1i comprising trans-1,3,3,3-tetrafluoro-1-propene (1234zeE) and said organic extracting agent, advantageously at the bottom of the distillation column.

Preferably, the stream G1i comprising trans-1,3,3,3-tetrafluoro-1-propene (1234zeE) and said organic extracting agent is separated out by distillation to form a stream G1j comprising said organic extracting agent and a stream G1k comprising trans-1,3,3,3-tetrafluoro-1-propene (1234zeE). The stream G1j comprising said organic extracting agent may be recycled into step b4). The stream G1k comprising trans-1,3,3,3-tetrafluoro-1-propene (1234zeE) may either be purified or destroyed by incineration.

Preferably, the stream G1h comprising 1,1,1,2,2-pentafluoropropane (245cb), preferably freed of trans-1,3,3,3-tetrafluoro-1-propene (1234zeE), is recycled into step a).

Alternatively, the process comprises a step b3'), subsequent to step b2), in which the stream G1c obtained in step b2) comprises 2,3,3,3-tetrafluoropropene (1234yf), 1,1,1,2,2-pentafluoropropane (245cb) and trans-1,3,3,3-tetrafluoro-1-propene (1234zeE); and said stream G1c is distilled to form a stream G1e' comprising 2,3,3,3-tetrafluoropropene (1234yf) and 1,1,1,2,2-pentafluoropropane (245cb) and a stream G1f comprising trans-1,3,3,3-tetrafluoro-1-propene (1234zeE). Said stream G1c is distilled by extractive distillation to form said stream G1e' comprising 2,3,3,3-tetrafluoropropene (1234yf) and 1,1,1,2,2-pentafluoropropane (245cb); and said stream G1f' comprising trans-1,3,3,3-tetrafluoro-1-propene (1234zeE). Thus, the stream G1c is distilled by extractive distillation according to the following steps:
- b4') placing said stream G1c obtained in step b2) in contact with an organic extracting agent to form a stream G1g', and
- b5') extractive distillation of the stream G1g' to form a stream G1e' comprising 2,3,3,3-tetrafluoropropene (1234yf) and 1,1,1,2,2-pentafluoropropane (245cb), advantageously at the top of the distillation column, and a stream G1h' comprising trans-1,3,3,3-tetrafluoro-1-propene (1234zeE) and said organic extracting agent, advantageously at the bottom of the distillation column.

Preferably, the stream G1e' comprising 2,3,3,3-tetrafluoropropene (1234yf) and 1,1,1,2,2-pentafluoropropane (245cb) may be subjected to subsequent purification steps. Thus, 2,3,3,3-tetrafluoropropene (1234yf) may be separated out, preferably by distillation of 1,1,1,2,2-pentafluoropropane (245cb) to form a stream comprising 2,3,3,3-tetrafluoropropene (1234yf) and a stream G1i' comprising 1,1,1,2,2-pentafluoropropane (245cb), said stream G1i' being recycled into step a). 2,3,3,3-tetrafluoropropene (1234yf) may also be subjected to subsequent purification steps so as to obtain a degree of purity sufficient for its marketing.

Preferably, the stream G1h' comprising trans-1,3,3,3-tetrafluoro-1-propene (1234zeE) and said organic extracting agent is separated out by distillation to form a stream G1j' comprising said organic extracting agent and a stream G1k' comprising trans-1,3,3,3-tetrafluoro-1-propene (1234zeE). The stream G1j' comprising said organic extracting agent may be recycled into step b4'). The stream G1k' comprising trans-1,3,3,3-tetrafluoro-1-propene (1234zeE) may either be purified or destroyed by incineration.

According to a preferred embodiment, said liquid stream L1 comprises, besides the unreacted HF, all or part of the intermediate products B and all or part of the side products C; and all or part of this stream L1 is brought to low temperature, advantageously between −50° C. and 15° C., preferably between −30° C. and 0° C., to form a first phase L1a comprising part of the unreacted HF and a second phase L1b comprising said intermediate products B and said side products C; optionally or not, said stream G1d formed in step b2) is mixed with the liquid stream L1 before said stream is brought to low temperature.

Preferably, said liquid stream L1 comprises part of the intermediate products B and all or part of the side products C, and all or part of the liquid stream L1 is brought to low temperature, advantageously between −50° C. and 20° C., to form a first phase L1a comprising part of the unreacted HF and a second phase L1b comprising said intermediate products B and said side products C; optionally or not, said stream G1d formed in step b2) is mixed with the liquid stream L1 before said stream is brought to low temperature.

Preferably, said first phase L1a is recycled into step a).

According to a preferred embodiment, said second phase L1b is distilled to recover a stream L1c comprising 1,1,1,2,2-pentafluoropropane (245cb) and trans-1,3,3,3-tetrafluoro-1-propene (1234zeE), advantageously at the top of the distillation column, and a stream L1d comprising 2-chloro-3,3,3-trifluoro-1-propene (1233xf), E-1-chloro-3,3,3-trifluoro-1-propene (1233zdE) and 1,1,1,3,3-pentafluoropropane (245fa), advantageously at the bottom of the distillation column; advantageously, said stream L1c is recycled into step a).

According to a preferred embodiment, said stream L1d is separated out to form a stream comprising 2-chloro-3,3,3-trifluoro-1-propene (1233xf) and a stream comprising E-1-chloro-3,3,3-trifluoro-1-propene (1233zdE) and 1,1,1,3,3-pentafluoropropane (245fa).

According to a preferred embodiment, the separation of said stream L1d is performed by extractive distillation.

According to a particular embodiment, the extractive distillation of said stream L1d comprises the steps of:
placing said stream L1d in contact with an organic extracting agent to form a composition L1e, and
extractive distillation of composition L1e to form a stream L1f comprising 2-chloro-3,3,3-trifluoro-1-propene (1233xf), advantageously at the top of the distillation column, and a stream L1g comprising E-1-chloro-3,3,3-trifluoro-1-propene (1233zdE) and 1,1,1,3,3-pentafluoropropane (245fa) and said organic extracting agent, advantageously at the bottom of the distillation column.

Preferably, the stream L1g is then separated out by distillation to form a stream L1h comprising said organic extracting agent and a stream L1i comprising E-1-chloro-3,3,3-trifluoro-1-propene (1233zdE) and 1,1,1,3,3-pentafluoropropane (245fa). The stream L1h may be recycled to be placed in contact with a stream L1d to form a composition L1e. The stream L1i comprising E-1-chloro-3,3,3-trifluoro-1-propene (1233zdE) and 1,1,1,3,3-pentafluoropropane (245fa) may either be purified or destroyed by incineration.

Preferably, the stream L1f comprising 2-chloro-3,3,3-trifluoro-1-propene (1233xf), preferably free of 1,1,1,3,3-pentafluoropropane (245fa) and E-1-chloro-3,3,3-trifluoro-1-propene (1233zdE), is recycled into step a).

According to a preferred embodiment, the present invention thus allows the recycling into step a) of one or more streams free of one or more side products C.

DETAILED DESCRIPTION OF THE INVENTION

Figure 1:
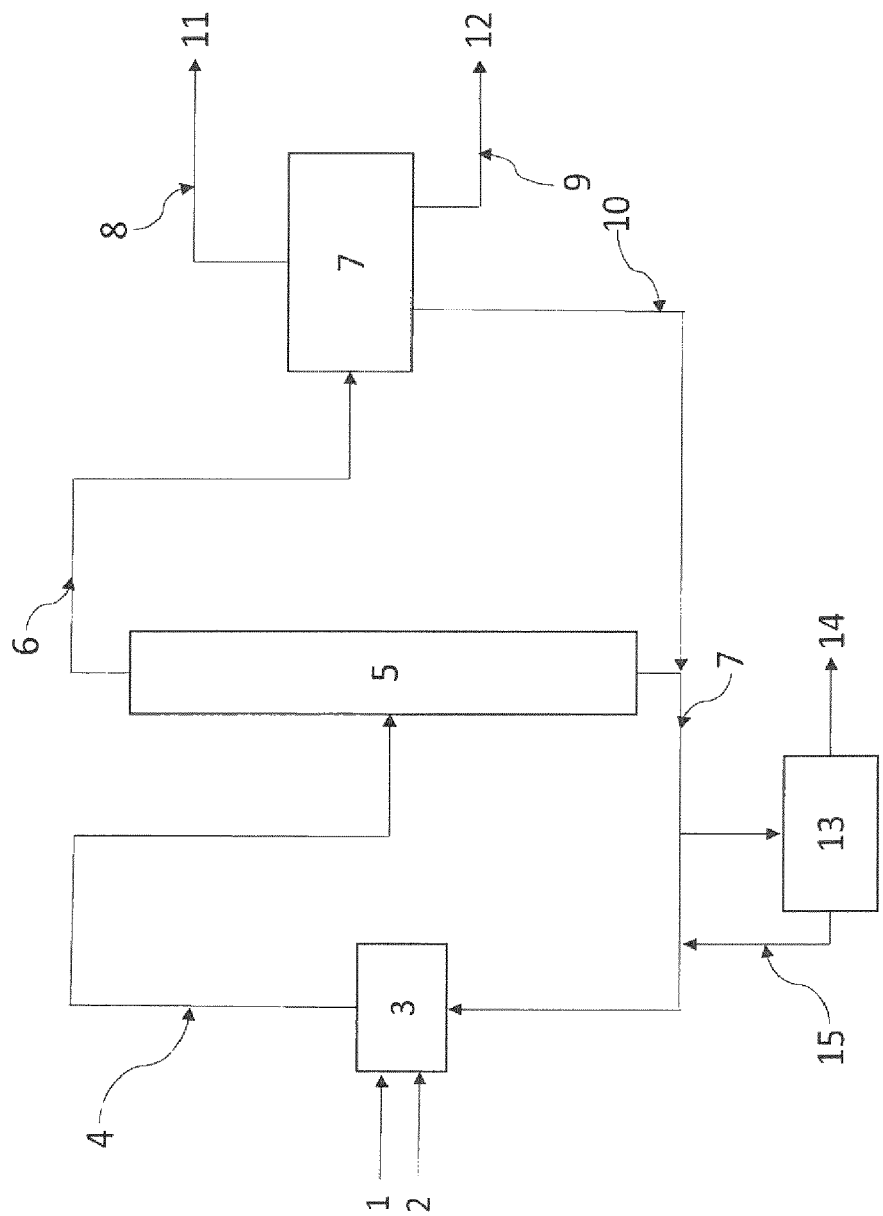
FIG. 1 schematically represents a device for performing a process for producing 2-3,3,3-tetrafluoro-1-propene according to a particular embodiment of the present invention.

The present invention allows the production and purification of 2,3,3,3-tetrafluoropropene (1234yf). According to a first aspect of the present invention, a process for producing and purifying 2,3,3,3-tetrafluoropropene (1234yf) is provided. Said process is performed using a starting composition comprising at least one compound of formula $CX(Y)_2$—$CX(Y)_m$—$CH_mXY$ (I) in which X and Y independently represent H, F or Cl and m=0 or 1; and/or fluorination in the presence of a catalyst of a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1.

Preferably, said process comprises the steps of:
a) placing the starting composition in contact, in the presence of a catalyst, with HF to produce a composition A comprising 2,3,3,3-tetrafluoropropene (1234yf), intermediate products B consisting of 2-chloro-3,3,3-trifluoropropene (1233xf), 1,1,1,2,2-pentafluoropropane (245cb), and side products C consisting of 1-chloro-3,3,3-trifluoro-1-propene (1233zd), 1,3,3,3-tetrafluoro-1-propene (1234ze) and 1,1,1,3,3-pentafluoropropane (245fa);
b) recovery of said composition A and purification thereof to form and recover a first stream comprising 2,3,3,3-tetrafluoropropene (1234yf) and one or more streams comprising 2-chloro-3,3,3-trifluoropropene (1233xf) and/or 1,1,1,2,2-pentafluoropropane (245cb);
c) recycling into step a) of said one or more streams comprising 2-chloro-3,3,3-trifluoropropene (1233xf) and/or 1,1,1,2,2-pentafluoropropane (245cb).

Preferably, the content of at least one of the side products C in said one or more streams recycled into step a) may be less than that in said composition A.

The content of any of the side products C may be reduced in one or more or all of said one or more streams recycled into step a). Preferably, said content of at least one of the side products C in said one or more streams recycled into step a) may be reduced by 20%, 30%, 40%, 50%, 60%, 70%, 80%, 90%, 95% or 98% relative to said content of the same at least one of the side products C in said composition A. Thus, the content of E-1-chloro-3,3,3-trifluoro-1-propene (1233zdE) in said one or more streams recycled into step a) may be reduced by 20%, 30%, 40%, 50%, 60%, 70%, 80%, 90%, 95% or 98% relative to the content of E-1-chloro-3,3,3-trifluoro-1-propene (1233zdE) in said composition A. According to another embodiment, the content of trans-1,3,3,3-tetrafluoro-1-propene (1234zeE) in said one or more streams recycled into step a) may be reduced by 20%, 30%, 40%, 50%, 60%, 70%, 80%, 90%, 95% or 98% relative to the content of trans-1,3,3,3-tetrafluoro-1-propene (1234zeE) in said composition A. According to another embodiment, the content of 1,1,1,3,3-pentafluoropropane (245fa) in said one or more streams recycled into step a) may be reduced by 20%, 30%, 40%, 50%, 60%, 70%, 80%, 90%, 95% or 98% relative to the content of 1,1,1,3,3-pentafluoropropane (245fa) in said composition A. The contents are expressed on a weight basis.

Said one or more streams recycled into step a) may be free of one or more side products C. The term "free of" means that the stream under consideration comprising less than 50 ppm, advantageously less than 20 ppm and preferably less than 10 ppm of the compound under consideration relative to the total weight of said stream.

According to a preferred embodiment, composition A also comprises HCl and some of the HF. Preferably, the purification of said composition A performed in step a b) comprises the distillation of said composition A to recover, at the top of the distillation column, a gaseous stream G1 comprising HCl and 2,3,3,3-tetrafluoropropene (1234yf); and, at the bottom of the distillation column, a liquid stream L1 comprising said part of the HF. All or some of the intermediate products B and all or some of the side products C may be contained in said gaseous stream G1 and/or in said liquid stream L1.

Preferably, all or some of the 1,1,1,2,2-pentafluoropropane (245cb) may be contained in said gaseous stream G1. All or some of the 1,1,1,2,2-pentafluoropropane (245cb) may also be contained in said liquid stream L1.

Preferably, all or some of the trans-1,3,3,3-tetrafluoro-1-propene (1234zeE) may be contained in said gaseous stream G1. All or some of the trans-1,3,3,3-tetrafluoro-1-propene (1234zeE) may also be contained in said liquid stream L1.

Preferably, all or some of the 2-chloro-3,3,3-trifluoropropene (1233xf) may be contained in said gaseous stream G1. All or some of the 2-chloro-3,3,3-trifluoropropene (1233xf) may also be contained in said liquid stream L1. Preferentially, the 2-chloro-3,3,3-trifluoropropene (1233xf) is contained in said liquid stream L; advantageously, 70%, 75%, 80%, 85% or 90% of the 2-chloro-3,3,3-trifluoropropene (1233xf) is contained in said liquid stream L1 relative to the gaseous stream G1.

Preferably, all or some of the E-1-chloro-3,3,3-trifluoro-1-propene (1233zdE) may be contained in said gaseous stream G1. All or some of the E-1-chloro-3,3,3-trifluoro-1-propene (1233zdE) may also be contained in said liquid stream L1. Preferentially, the E-1-chloro-3,3,3-trifluoro-1-propene (1233zdE) is contained in said liquid stream L; advantageously, 70%, 75%, 80%, 85%, 90% or 95% of the 1-chloro-3,3,3-trifluoro-1-propene (1233zd) is contained in said liquid stream L1 relative to the gaseous stream G1.

Preferably, all or some of the 1,1,1,3,3-pentafluoropropane (245fa) may be contained in said gaseous stream G1. All or some of the 1,1,1,3,3-pentafluoropropane (245fa) may also be contained in said liquid stream L1. Preferentially, the 1,1,1,3,3-pentafluoropropane (245fa) is contained in said liquid stream L; advantageously, 70%, 75%, 80%, 85%, 90% or 95% of the 1,1,1,3,3-pentafluoropropane (245fa) is contained in said liquid stream L1 relative to the gaseous stream G1.

According to a preferred embodiment, said gaseous stream G1 comprises part of the intermediate products B and part of the side products C, and said gaseous stream G1 is purified via the following steps:
  b1) distillation of the gaseous stream G1 to recover a stream G1a comprising HCl, advantageously at the top of the distillation column, and a stream G1b comprising 2,3,3,3-tetrafluoropropene (1234yf), said part of the intermediate products B and said part of the side products C, advantageously at the bottom of the distillation column;
  b2) distillation of said stream G1b obtained in step b1) to form a stream G1c comprising 2,3,3,3-tetrafluoropropene (1234yf), a portion of said part of the intermediate products B and a portion of said part of the side products C, advantageously at the top of the distillation column, and a stream G1d comprising a portion of said part of the intermediate products B and a portion of said part of the side products C, advantageously at the bottom of the distillation column.

Preferably, the stream G1c formed in step b2) may comprise 2,3,3,3-tetrafluoropropene (1234yf), 1,1,1,2,2-pentafluoropropane (245cb) and 1,3,3,3-tetrafluoro-1-propene (1234ze). Preferably, the stream G1d formed in step b2) may comprise 1,1,1,2,2-pentafluoropropane (245cb), trans-1,3,3,3-tetrafluoro-1-propene (1234zeE) and 2-chloro-3,3,3-trifluoropropene (1233xf) and optionally or not E-1-chloro-3,3,3-trifluoro-1-propene (1233zdE) and 1,1,1,3,3-pentafluoropropane (245fa). In particular, the content of 1,1,1,2,2-pentafluoropropane (245cb) is greater in stream G1d than in stream G1c. The stream G1d may contain 55%, 60%, 65%, 70%, 75%, 78% or 80% of 1,1,1,2,2-pentafluoropropane (245cb) relative to the total content of 1,1,1,2,2-pentafluoropropane (245cb) in stream G d and G1c.

The stream G1d may be recycled into step a) of the present process. The stream G1d may be one of said one or more streams recycled into step a) (step c) of the present process.

Thus, the present process may be a process for producing and purifying 2,3,3,3-tetrafluoropropene (1234yf) which is performed using a starting composition comprising at least one compound of formula $CX(Y)_2—CX(Y)_m—CH_mXY$ (I) in which X and Y independently represent a hydrogen, fluorine or chlorine atom and m=0 or 1; and/or fluorination, in the presence of a catalyst, of a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1; said process comprising the steps of:
  a) placing the starting composition in contact, in the presence of a catalyst, with HF to produce a composition A comprising HCl, part of the unreacted HF, 2,3,3,3-tetrafluoropropene (1234yf), intermediate products B consisting of 2-chloro-3,3,3-trifluoropropene (1233xf), 1,1,1,2,2-pentafluoropropane (245cb), and side products C consisting of E-1-chloro-3,3,3-trifluoro-1-propene (1233zdE), trans-1,3,3,3-tetrafluoro-1-propene (1234zeE) and 1,1,1,3,3-pentafluoropropane (245fa);
  b) recovery of said composition A and distillation thereof to form and recover, at the top of the distillation column, a gaseous stream G1 comprising HCl and 2,3,3,3-tetrafluoropropene (1234yf), part of the intermediate products B and part of the side products C; and, at the bottom of the distillation column, a liquid stream L1 comprising part of the unreacted HF, part of the intermediate products B and part of the side products C; said gaseous stream G1 being purified via the following steps:
    b1) distillation of the gaseous stream G1 to recover a stream G1a comprising HCl and a stream G1b comprising 2,3,3,3-tetrafluoropropene (1234yf), said part of the intermediate products B and said part of the side products C;
    b2) distillation of said stream G1b obtained in step b1) to form a stream G1c comprising 2,3,3,3-tetrafluoropropene (1234yf), a portion of said part of the intermediate products B and a portion of said part of the side products C and a stream G1d comprising a portion of said part of the intermediate products B and a portion of said part of the side products C;
  c) recycling into step a) of the stream G1d;
  preferably, the content of at least one of the side products C in the stream G1d being less than that in said composition A.

According to a preferred embodiment, the process comprises a step b3), subsequent to step b2), in which the stream G1c obtained in step b2) comprises 2,3,3,3-tetrafluoropropene (1234yf), 1,1,1,2,2-pentafluoropropane (245cb) and trans-1,3,3,3-tetrafluoro-1-propene (1234zeE); and said stream G1c is distilled to form a stream G1e comprising 2,3,3,3-tetrafluoropropene (1234yf) and a stream G1f comprising 1,1,1,2,2-pentafluoropropane (245cb) and trans-1,3,3,3-tetrafluoro-1-propene (1234zeE).

The stream G1f obtained in step b3) may be separated out by extractive distillation.

According to a particular embodiment, the stream G1f obtained in step b3) is separated out by extractive distillation according to the following steps:
- b4) placing said stream G1f obtained in step b3) in contact with an organic extracting agent to form a stream G1g, and
- b5) extractive distillation of the stream G1g to form a stream G1h comprising 1,1,1,2,2-pentafluoropropane (245cb), advantageously at the top of the distillation column, and a composition G1i comprising trans-1,3,3,3-tetrafluoro-1-propene (1234zeE) and said organic extracting agent, advantageously at the bottom of the distillation column.

Preferably, the stream G1i comprising trans-1,3,3,3-tetrafluoro-1-propene (1234zeE) and said organic extracting agent is separated out by distillation to form a stream G1j comprising said organic extracting agent and a stream G1k comprising trans-1,3,3,3-tetrafluoro-1-propene (1234zeE). The stream G1j comprising said organic extracting agent may be recycled into step b4). The stream G1k comprising trans-1,3,3,3-tetrafluoro-1-propene (1234zeE) may either be purified or destroyed by incineration.

According to a preferred embodiment, said organic extracting agent is a solvent chosen from the group consisting of halohydrocarbon, alcohol, ketone, amine, ester, ether, aldehyde, nitrile, carbonate, thioalkyl, amide and heterocycle. Advantageously, said organic extracting agent is a solvent chosen from the group consisting of alcohol, ketone, amine, ester and heterocycle. According to a preferred embodiment, said organic extracting agent has a boiling point of between 10 and 150° C.

Preferably, said extracting agent may have a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane in said organic extracting agent at infinite dilution;

P1 represents the saturating vapor pressure of 1,1,1,2,2-pentafluoropropane;

$\gamma_{2,S}$ represents the activity coefficient of said trans-1,3,3,3-tetrafluoro-1-propene (1234zeE) in said organic extracting agent at infinite dilution;

P2 represents the saturating vapor pressure of said trans-1,3,3,3-tetrafluoro-1-propene (1234zeE);

advantageously, the separation factor is greater than or equal to 1.2, preferably greater than or equal to 1.4, more preferentially greater than or equal to 1.6, in particular greater than or equal to 1.8, more particularly greater than or equal to 2.0.

The saturating vapor pressure is considered for a temperature of 25° C.

Preferably, said organic extracting agent may have a separation capacity $C_{2,S}$ of greater than or equal to 0.20, said separation capacity being calculated by the formula $C_{2,S}=1/(\gamma_{2,S})$ in which $\gamma_{2,S}$ represents the activity coefficient of said trans-1,3,3,3-tetrafluoro-1-propene (1234zeE) in said organic extracting agent at infinite dilution;

advantageously, the separation capacity $C_{2,S}$ is greater than or equal to 0.40, preferably greater than or equal to 0.60, more preferentially greater than or equal to 0.80, in particular greater than or equal to 1.0.

Preferably, said organic extracting agent may have a separation factor $S_{1,2}$ of greater than or equal to 1.5 and an absorption capacity $C_{2,S}$ of greater than or equal to 0.6 and may be chosen from the group consisting of ethylamine, acetaldehyde, isopropylamine, methyl formate, diethyl ether, 1,2-epoxypropane, ethylmethylamine, dimethoxymethane, 2-amino-2-methylpropane, methyl cyclopropyl ether, n-propylamine, isopropylmethylamine, 2-ethoxypropane, methyl t-butyl ether, diethylamine, propanone, methyl acetate, 4-methoxy-2-methyl-2-butanethiol, 2-butanamine, n-methylpropylamine, isobutanal, tetrahydrofuran, isopropyl formate, diisopropyl ether, 2-ethoxy-2-methylpropane, 1-butylamine, ethyl acetate, butanone, n-propyl formate, 2-ethoxybutane, 1-methoxy-2-methylbutane, 2,2-dimethoxypropane, 1-ethoxy-2-methylpropane, diisopropylamine, 1,2-dimethoxyethane, 3-methyl-2-butanamine, diethoxymethane, isopropyl acetate, di-n-propyl ether, 3-pentylamine, n-methylbutylamine, 1-ethoxybutane, 1-methoxy-2-propanamine, 2-methylbutanal, 2-methoxyethanamine, tert-butyl acetate, propionitrile, 2-allyloxyethanol, 1-methoxypentane, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, dipropylamine, 2-ethoxyethanamine, sec-butyl acetate, n-methyl-1,2-ethanediamine, 2,2-diethoxypropane, pyridine, 4-methyl-2-pentanone, 1,2-diaminoethane, butyronitrile, sec-butyl tert-butyl ether, 1-methoxy-2-propanol, 1,2-propanediamine, 2,6-dimethyl-5-heptenal, 1-(dimethylamino)-2-propanol, 3-methyl-3-pentanol, 1,1-diethoxypropane, 2-ethylbutylamine, diethyl carbonate, n-butyl acetate, 2-hexanone, n-ethylethylenediamine, 5-hexen-2-one, 2-methylpyridine, 2-methoxy-1-propanol, hexanal, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-methylpyrazine, 2-ethoxy-1-propanol, 1-methylpiperazine, 1,3-propanediamine, di-n-butyl ether, valeronitrile, 2-heptanamine, 1-ethoxyhexane, n,n-diethylethylenediamine, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol and 1-propoxy-2-propanol. Advantageously, said organic extracting agent may have a separation factor $S_{1,2}$ of greater than or equal to 1.8 and/or an absorption capacity $C_{2,S}$ of greater than or equal to 0.8; and may be chosen from the group consisting of ethylamine, isopropylamine, ethylmethylamine, 2-amino-2-methylpropane, n-propylamine, isopropylmethylamine, diethylamine, propanone, 2-butanamine, n-methylpropylamine, tetrahydrofuran, 1-butylamine, ethyl acetate, butanone, 1,2-dimethoxyethane, 3-methyl-2-butanamine, 3-pentylamine, n-methylbutylamine, 1-methoxy-2-propanamine, 2-methoxyethanamine, ethyl propionate, dioxane, 3-pentanone, 2-pentanone, 2-methoxy-1-propanamine, trimethoxymethane, n-pentylamine, 3,3-dimethyl-2-butanone, 1,3-dioxane, piperidine, 2-ethoxyethanamine, n-methyl-1,2-ethanediamine, 1,2-diaminoethane, butyronitrile, 1-methoxy-2-propanol, 1,2-propanediamine, 1-(dimethylamino)-2-propanol, 2-ethylbutylamine, diethyl carbonate, n-butyl acetate, 2-hexanone, n-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, 2-ethoxy-1-propanol, 1-methylpiperazine, 1,3-propanediamine, valeronitrile, 2-heptanamine, n,n-diethylethylenediamine, 4-methyl-2-hexanone, 1-methoxy-2-acetoxypropane, 4-methylpyridine, n,n'-diethyl-1,2-ethanediamine, 2,6-dimethylmorpholine, methyl hexanoate, 2-propoxyethanol and 1-propoxy-2-propanol. Preferably, said organic extracting agent may have a separation factor $S_{1,2}$ of greater than or equal to 1.9 and/or an absorption capacity $C_{2,S}$ of greater than or equal to 0.9 and may be chosen from the group consisting of ethylamine, isopropylamine, ethylmethylamine, 2-amino-2-methylpropane, n-propylamine, isopropylmethylamine, diethylamine, propanone, 2-butanamine, n-methylpropylamine, tetrahydrofuran, 1-butylamine, ethyl acetate, butanone, 1,2-dimethoxyethane, 3-methyl-2-butanamine, 3-pentylamine, n-methylbutylamine, 1-methoxy-2-propanamine, 2-methoxyethanamine, ethyl propionate, dioxane, 3-pentanone, 2-pentanone, 2-methoxy-1-propanamine, n-pentylamine, 3,3-dimethyl-2-butanone, 1,3-dioxane, piperidine, 2-ethoxyethanamine, n-methyl-1,2-ethanediamine, 1,2-diaminoethane, 1,2-propanediamine, 1-(dimethylamino)-2-propanol, 2-ethylbutylamine, n-butyl acetate, 2-hexanone, n-ethylethylenediamine, 1-ethoxy-2-propanol, 4-methyl-2-hexanamine, hexylamine, 2-(dimethylamino)ethanol, cyclohexylamine, n-ethyl-2-dimethylaminoethylamine, 2-ethoxy-1-propanol, 1-methylpiperazine, 1,3-propanediamine, 2-heptanamine, n,n-diethylethylenediamine, 1-methoxy-2-acetoxypropane, 4-methylpyridine, n,n'-diethyl-1,2-ethanediamine, 2,6-dimethylmorpholine, methyl hexanoate and 1-propoxy-2-propanol. More particularly, said organic extracting agent is chosen from the group consisting of ethylamine, isopropylamine, n-propylamine, diethylamine, propanone, tetrahydrofuran, ethyl acetate, butanone, 3-pentylamine, 2-methoxyethanamine, dioxane, 3-pentanone, 2-pentanone, n-pentylamine, 1,3-dioxane, 1,2-diaminoethane, 1,2-propanediamine, 2-methoxyethanol, n-butyl acetate and 1-ethoxy-2-propanol.

Said stream G1h comprising 1,1,1,2,2-pentafluoropropane (245cb) may be recycled into step a) of the present process. Said stream G1h comprising 1,1,1,2,2-pentafluoropropane (245cb) may be one of said one or more streams recycled into step a) of the present process (step c)).

As explained above, the stream G1i comprising trans-1,3,3,3-tetrafluoro-1-propene (1234zeE) and said organic extracting agent is distilled to separate the organic extracting agent from the trans-1,3,3,3-tetrafluoro-1-propene (1234zeE); advantageously, said organic extracting agent thus separated out is recycled into step b4). The trans-1,3,3,3-tetrafluoro-1-propene (1234zeE) may thus be incinerated or purified to be used subsequently or to be sold.

The stream G1e may be purified, for example by extractive distillation, to remove the trans-1,3,3,3-tetrafluoro-1-propene (1234ze-E) that may be present. In this case, said organic extracting agent is a solvent chosen from the group consisting of hydrocarbon, halohydrocarbon, alcohol, ketone, amine, ester, ether, aldehyde, nitrile, carbonate, thioalkyl, amide and heterocycle; or said organic extracting agent is difluorodiethylsilane, triethylfluorosilane or perfluorobutanoic acid; preferably from the group consisting of amine, ether, ketone, ester, alcohol, aldehyde and heterocycle. The boiling point of said organic extract agent may be between 10 and 150° C. Said organic extract agent may have a separation factor $S_{1,2}$ of greater than or equal to 1.1, said separation factor being calculated by the formula $S_{1,2}=(\square_{1,S}*P1)/(\square_{2,S}*P2)$ in which $\square_{1,S}$ represents the activity coefficient of 2,3,3,3-tetrafluoro-1-propene in said organic extracting agent at infinite dilution, P1 represents the saturating vapor pressure of 2,3,3,3-tetrafluoro-1-propene, $\square_{2,S}$ represents the activity coefficient of trans-1,3,3,3-tetrafluoro-1-propene (1234ze-E) in said organic extracting agent at infinite dilution and P2 represents the saturating vapor pressure of said at least one of the compounds consisting of trans-1,3,3,3-tetrafluoro-1-propene (1234ze-E); advantageously, the separation factor is greater than or equal to 1.2, preferably greater than or equal to 1.4, more preferentially greater than or equal to 1.6, in particular greater than or equal to 1.8 and more particularly greater than or equal to 2.0. Said organic extracting agent may have an absorption capacity $C_{2,S}$ of greater than or equal to 0.20, said absorption capacity being calculated by the formula $C_{2,S}=1/(\square_{2,S})$ in which $\square_{2,S}$ represents the activity coefficient of trans-1,3,3,3-tetrafluoro-1-propene (1234ze-E) in said organic extracting agent at infinite dilution; advantageously, the absorption capacity $C_{2,S}$ is greater than or equal to 0.40, preferably greater than or equal to 0.60, more preferentially greater than or equal to 0.80, in particular greater than or equal to 1.0. Advantageously, said organic extracting agent may be chosen from the group consisting of ethylamine, isopropylamine, diethyl ether, ethoxyethene, dimethoxymethane, n-propylamine, methyl t-butyl ether, diethylamine, propanone, methyl acetate, isobutanal, tetrahydrofuran, isopropyl formate, diisopropyl ether, 2-ethoxy-2-methylpropane, ethyl acetate, butanone, diethoxymethane, isopropyl acetate, 3-pentylamine, 2-methoxyethanamine, tert-butyl acetate, dioxane, 3-pentanone, 1,1-diethoxyethane, 2-pentanone, trimethoxymethane, n-pentylamine, 1,3-dioxane, 3,3-dimethyl-2-butanone, sec-butyl acetate, 4-methyl-2-pentanone, 1,2-diaminoethane, 1-methoxy-2-propanol, diethyl carbonate, n-butyl acetate, 1-ethoxy-2-propanol and hexanal; advantageously, said organic extracting agent is chosen from the group consisting of ethylamine, isopropylamine, diethyl ether, dimethoxymethane, n-propylamine, diethylamine, diisopropyl ether, 2-ethoxy-2-methylpropane, butanone, diethoxymethane, isopropyl acetate, 3-pentylamine, 2-methoxyethanamine, tert-butyl acetate, dioxane, trimethoxymethane, n-pentylamine, 1,3-dioxane, sec-butyl acetate, 1,2-diaminoethane, 1-methoxy-2-propanol, n-butyl acetate, 1-ethoxy-2-propanol and hexanal; preferably, said organic extracting agent is chosen from the group consisting of ethylamine, isopropylamine, diethyl ether, dimethoxymethane, n-propylamine, diethylamine, diisopropyl ether, 2-ethoxy-2-methylpropane, diethoxymethane, isopropyl acetate, 3-pentylamine, 2-methoxyethanamine, tert-butyl acetate, dioxane, trimethoxymethane, n-pentylamine, 1,3-dioxane, sec-butyl acetate, 1,2-diaminoethane, 1-methoxy-2-propanol, n-butyl acetate, 1-ethoxy-2-propanol and hexanal.

Alternatively, as mentioned above, the process comprises a step b3'), subsequent to step b2), in which the stream G1c obtained in step b2) comprises 2,3,3,3-tetrafluoropropene (1234yf), 1,1,1,2,2-pentafluoropropane (245cb) and trans-1,3,3,3-tetrafluoro-1-propene (1234zeE); and said stream G1c is distilled to form a stream G1e' comprising 2,3,3,3-tetrafluoropropene (1234yf) and 1,1,1,2,2-pentafluoropropane (245cb) and a stream G1f comprising trans-1,3,3,3-tetrafluoro-1-propene (1234zeE). Thus, the stream G1c may be distilled by extractive distillation according to the following steps:

b4') placing said stream G1c obtained in step b2) in contact with an organic extracting agent to form a stream G1g', and b5') extractive distillation of the stream G1g' to form the stream G1e' comprising 2,3,3,3-tetrafluoropropene (1234yf) and 1,1,1,2,2-pentafluoropropane (245cb), advantageously at the top of the distillation column, and the stream G1h' comprising trans-1,3,3,3-tetrafluoro-1-propene (1234zeE) and said organic extracting agent, advantageously at the bottom of the distillation column.

According to a preferred embodiment, said organic extracting agent may have a separation factor $S_{1,2}$ of greater than or equal to 1.1, said separation factor being calculated by the formula $S_{1,2}=(\square_{1,S}*P1)/(\square_{2,S}*P2)$ in which $\square_{1,S}$ represents the activity coefficient of 2,3,3,3-tetrafluoro-1-propene in said organic extracting agent at infinite dilution, P1 represents the saturating vapor pressure of 2,3,3,3-tetrafluoro-1-propene, $\square_{2,S}$ represents the activity coefficient of trans-1,3,3,3-tetrafluoro-1-propene (1234ze-E) in said organic extracting agent at infinite dilution and P2 represents the saturating vapor pressure of trans-1,3,3,3-tetrafluoro-1-propene (1234ze-E); advantageously, the separation factor is greater than or equal to 1.2, preferably greater than or equal to 1.4, more preferentially greater than or equal to 1.6 and in particular greater than or equal to 1.8. In this embodiment, said organic extracting agent may also have a separation factor $S_{1,2}$ of greater than or equal to 1.1, said separation factor being calculated by the formula $S_{1,2}=(\square_{1,S}*P1)/(\square\square_{2,S}*P2)$ in which $\square_{1,S}$ represents the activity coefficient of 1,1,1,2,2-pentafluoropropane (245cb) in said organic extracting agent at infinite dilution, P1 represents the saturating vapor pressure of 1,1,1,2,2-pentafluoropropane (245cb), $\square_{2,S}$ represents the activity coefficient of trans-1,3,3,3-tetrafluoro-1-propene (1234ze-E) in said organic extracting agent at infinite dilution and P2 represents the saturating vapor pressure of trans-1,3,3,3-tetrafluoro-1-propene (1234ze-E); advantageously, the separation factor is greater than or equal to 1.2, preferably greater than or equal to 1.4, more preferentially greater than or equal to 1.6 and in particular greater than or equal to 1.8, more particularly greater than or equal to 2.0. In this preferred embodiment, said organic extracting agent may have an absorption capacity $C_{2,S}$ of greater than or equal to 0.20, said absorption capacity being calculated by the formula $C_{2,S}=1/(\square_{2,S})$ in which $\square_{2,S}$ represents the activity coefficient of said at least one compound consisting of trans-1,3,3,3-tetrafluoro-1-propene (1234ze-E) in said organic extracting agent at infinite dilution; preferably, $\square_{2,S}$ represents the activity coefficient of said at least one compound consisting of trans-1,3,3,3-tetrafluoro-1-propene (1234ze-E) in said organic extracting agent at infinite dilution; advantageously, the absorption capacity $C_{2,S}$ is greater than or equal to 0.40, preferably greater than or equal to 0.60, more preferentially greater than or equal to 0.80, in particular greater than or equal to 1.0. Thus, in this preferred embodiment, said organic extracting agent may be ethylamine, isopropylamine, diethyl ether, ethylmethylamine, 2-amino-2-methylpropane, n-propylamine, isopropylmethylamine, 2-ethoxypropane, methyl t-butyl ether, diethylamine, propanone, methyl acetate, 2-butanamine, n-methylpropylamine, isobutanal, tetrahydrofuran, 1-butylamine, ethyl acetate, butanone, n-propyl formate, 2,2-dimethoxypropane, 1-ethoxy-2-methylpropane, 1,2-dimethoxyethane, 3-methyl-2-butanamine, diethoxymethane, isopropyl acetate, 3-pentylamine, n-methylbutylamine, 1-ethoxybutane, 1-methoxy-2-propanamine, 2-methylbutanal, 2-methoxyethanamine, tert-butyl acetate, 1-methoxypentane, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, 1,1-diethoxypropane, 2-ethylbutylamine, diethyl carbonate, n-butyl acetate, 2-hexanone, n-ethylethylenediamine, 5-hexen-2-one, 2-methylpyridine, 2-methoxy-1-propanol or hexanal; advantageously ethylamine, isopropylamine, diethyl ether, n-propylamine, diethylamine, propanone, methyl acetate, butanone, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol or hexanal; preferably ethylamine, isopropylamine, diethyl ether, n-propylamine, diethylamine, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol or hexanal.

Preferably, the stream G1e' comprising 2,3,3,3-tetrafluoropropene (1234yf) and 1,1,1,2,2-pentafluoropropane (245cb) may be subjected to subsequent purification steps. Thus, 2,3,3,3-tetrafluoropropene (1234yf) may be separated out, preferably by distillation of 1,1,1,2,2-pentafluoropropane (245cb) to form a stream comprising 2,3,3,3-tetrafluoropropene (1234yf) and a stream G1i' comprising 1,1,1,2,2-pentafluoropropane (245cb), said stream G1i' being recycled into step a). 2,3,3,3-Tetrafluoropropene (1234yf) may also be subjected to subsequent purification steps so as to obtain a degree of purity sufficient for its marketing. For example, it may be purified by extractive distillation, to remove the trans-1,3,3,3-tetrafluoro-1-propene (1234ze-E) that may be present.

Preferably, the stream G1h' comprising trans-1,3,3,3-tetrafluoro-1-propene (1234zeE) and said organic extracting agent is separated out by distillation to form a stream G1j' comprising said organic extracting agent and a stream G1k' comprising trans-1,3,3,3-tetrafluoro-1-propene (1234zeE). The stream G1j' comprising said organic extracting agent may be recycled into step b4'). The stream G1k' comprising trans-1,3,3,3-tetrafluoro-1-propene (1234zeE) may either be purified or destroyed by incineration.

If the gaseous stream G1 optionally comprises HF after distillation, said HF may be contained in said stream G1b, and then G1c. Thus, prior to step b3), the unreacted HF contained in the stream G1c may be removed from said stream G1c. Removal of the HF may be performed via a series of steps of absorption of said HF in aqueous medium. The stream G1c may then be neutralized in the presence of a base, for example an alkali metal or alkaline-earth metal hydroxide, and then dried, for example over molecular sieves to remove any traces of water.

Optionally or not, if the stream G1c comprises impurities with a boiling point below that of the 2,3,3,3-tetrafluoro-1-propene, they may be removed by distillation. Said impurities with a boiling point below the boiling point of 2,3,3,3-tetrafluoro-1-propene may be trifluoromethane (F23), monofluoromethane (F41), difluoromethane (F32), pentafluoroethane (F125), 1,1,1-trifluoroethane (F143a), trifluoropropyne or 1-chloro-pentafluoroethane (F115); and these impurities may be recovered at the top of the distillation column. The stream recovered at the bottom of the distillation column may then be used as described above for the stream G1c in step b) and the subsequent steps.

According to another preferred embodiment, said liquid stream L1 comprises all or some of the intermediate products B and all or some of the side products C; and all or some of this stream L1 is brought to low temperature, advantageously between −50° C. and 20° C., to form a first phase L1a comprising part of the unreacted HF and a second phase L1b comprising said intermediate products B and said side products C. Thus, said liquid stream L1 may comprise part of the intermediate products B and part of the side products C; and all or some of this stream L1 is brought to low temperature, advantageously between −50° C. and 20° C., to form a first phase L1a comprising part of the unreacted HF and a second phase L1b comprising said intermediate products B and said side products C. Advantageously, said low temperature is between −50° C. and 15° C., preferably between −40° C. and 10° C., in particular between −30° C. and 0° C. This step may be performed in continuous or batch mode.

Said first phase L1a may be recycled into step a).

Optionally or not, said stream G1d formed in step b2) may be mixed with the liquid stream L1 before all or some of said stream is brought to low temperature.

All or some of the 1,1,1,2,2-pentafluoropropane (245cb) may also be contained in said liquid stream L1 and then in said second phase L1b.

All or some of the 1,3,3,3-tetrafluoro-1-propene (1234ze) may also be contained in said liquid stream L1 and then in said second phase L1b.

All or some of the 2-chloro-3,3,3-trifluoropropene (1233xf) may also be contained in said liquid stream L1 and then in said second phase L1b.

All or some of the E-1-chloro-3,3,3-trifluoro-1-propene (1233zdE) may also be contained in said liquid stream L1 and then in said second phase L1b.

All or some of the 1,1,1,3,3-pentafluoropropane (245fa) may also be contained in said liquid stream L1 and then in said second phase L1b.

Preferably, said second phase L1b may comprise 1,1,1,3,3-pentafluoropropane (245fa), E-1-chloro-3,3,3-trifluoro-1-propene (1233zdE), 2-chloro-3,3,3-trifluoropropene (1233xf), 1,3,3,3-tetrafluoro-1-propene (1234ze) and 1,1,1,2,2-pentafluoropropane (245cb).

According to a preferred embodiment, said second phase L1b is distilled to recover a stream L1c comprising 1,1,1,2,2-pentafluoropropane (245cb) and 1,3,3,3-tetrafluoro-1-propene (1234ze), advantageously at the top of the distillation column, and a stream L1d comprising 2-chloro-3,3,3-trifluoro-1-propene (1233xf), E-1-chloro-3,3,3-trifluoro-1-propene (1233zdE) and 1,1,1,3,3-pentafluoropropane (245fa); advantageously at the bottom of the distillation column. Said stream L1c may be recycled into step a). The stream L1c may thus be one of said one or more streams recycled into step a) during step c) of the present process. Optionally, said stream L1c may be purified to separate 1,1,1,2,2-pentafluoropropane (245cb) and 1,3,3,3-tetrafluoro-1-propene (1234ze). This may be performed by extractive distillation as explained above in relation with the separation of the stream G1f.

According to a preferred embodiment, said stream L1d may be separated out to form a stream comprising 2-chloro-3,3,3-trifluoro-1-propene (1233xf) and a stream comprising E-1-chloro-3,3,3-trifluoro-1-propene (1233zdE) and 1,1,1,3,3-pentafluoropropane (245fa). The separation of said stream L1d may be performed by extractive distillation.

Preferably, said stream L1d may be an azeotropic or quasi-azeotropic composition comprising 2-chloro-3,3,3-trifluoro-1-propene (1233xf), E-1-chloro-3,3,3-trifluoro-1-propene (1233zdE) and 1,1,1,3,3-pentafluoropropane (245fa).

Preferably, said separation may be performed by extractive distillation. Said extractive distillation of said stream L1d comprises the steps of:
 placing said stream L1d in contact with an organic extracting agent to form a composition L1e, and
 extractive distillation of composition L1e to form a stream L1f comprising 2-chloro-3,3,3-trifluoro-1-propene (1233xf), advantageously at the top of the distillation column, and a stream L1g comprising E-1-chloro-3,3,3-trifluoro-1-propene (1233zdE) and 1,1,1,3,3-pentafluoropropane (245fa) and said organic extracting agent, advantageously at the bottom of the distillation column.

Preferably, the stream L1g is then separated out by distillation to form a stream L1h comprising said organic extracting agent and a stream L1i comprising E-1-chloro-3,3,3-trifluoro-1-propene (1233zdE) and 1,1,1,3,3-pentafluoropropane (245fa). The stream L1h may be recycled to be placed in contact with a stream L1d to form a composition L1e. The stream L1i comprising E-1-chloro-3,3,3-trifluoro-1-propene (1233zdE) and 1,1,1,3,3-pentafluoropropane (245fa) may either be purified or destroyed by incineration.

According to a preferred embodiment, said organic extracting agent placed in contact with the stream L1d is a solvent chosen from the group consisting of hydrocarbon, halohydrocarbon, alcohol, ketone, amine, ester, ether, aldehyde, nitrile, carbonate, sulfoxide, sulfate, thioalkyl, amide, heterocycle and phosphate or the organic extracting agent is perfluorobutanoic acid. According to a preferred embodiment, said organic extracting agent has a boiling point of between 50 and 200° C. According to a preferred embodiment, said organic extracting agent has a separation factor $S_{1,2}$ of greater than or equal to 1.1, said separation factor being calculated by the formula $S_{1,2}=(\square_{1,S}*P1)/(\square_{2,S}*P2)$ in which $\square_{1,S}$ represents the activity coefficient of 2-chloro-3,3,3-trifluoropropene in said organic extracting agent at infinite dilution;

P1 represents the saturating vapor pressure of 2-chloro-3,3,3-trifluoropropene;

$\square_{2,S}$ represents the activity coefficient of 1,1,1,3,3-pentafluoropropane (245fa) in said organic extracting agent at infinite dilution;

P2 represents the saturating vapor pressure of 1,1,1,3,3-pentafluoropropane (245fa);

advantageously, the separation factor $S_{1,2}$ is greater than or equal to 1.2, preferably greater than or equal to 1.4, more preferentially greater than or equal to 1.6, in particular greater than or equal to 1.8, more particularly greater than or equal to 2.0;

and said organic extracting agent has an absorption capacity $C_{2,S}$ of greater than or equal to 0.20, the absorption capacity being calculated by the formula $C_{2,S}=1/(\square_{2,S})$ in which $\square_{2,S}$ represents the activity coefficient of 1,1,1,3,3-pentafluoropropane (245fa) in said organic extracting agent at infinite dilution; advantageously, the absorption capacity $C_{2,S}$ is greater than or equal to 0.40, preferably greater than or equal to 0.60, more preferentially greater than or equal to 0.80, in particular greater than or equal to 1.0.

Thus, according to a particular embodiment, said organic extracting agent may be chosen from the group consisting of ethanedial, propanone, methyl acetate, methylglyoxal, ethyl acetate, butanone, propionitrile, dioxane, trimethoxymethane, 1,3-dioxane, 1,3,5-trioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, methyl acetoacetate, n,n-dimethylpropanamide, dimethyl malonate, diethyl sulfoxide, 2-(2-methoxyethoxy)ethanol, trimethyl phosphate and diethyl malonate; preferably, said organic extracting agent may be chosen from the group consisting of propanone, methyl acetate, ethyl acetate, butanone, dioxane, trimethoxymethane, 1,3-dioxane, 1,3,5-trioxane, 1,2-diaminoethane and 1-methoxy-2-propanol. Preferably, this particular embodiment may allow efficient separation of 2-chloro-3,3,3-trifluoropropene and 1,1,1,3,3-pentafluoropropane (245fa).

According to a particular embodiment, said organic extracting agent placed in contact with the stream L1d may have a separation factor $S_{1,2}$ of greater than or equal to 1.1, said separation factor being calculated by the formula $S_{1,2} = (\gamma_{1,S} * P1)/(\gamma_{2,S} * P2)$ in which
- $\gamma_{1,S}$ represents the activity coefficient of 2-chloro-3,3,3-trifluoropropene in said organic extracting agent at infinite dilution;
- P1 represents the saturating vapor pressure of 2-chloro-3,3,3-trifluoropropene;
- $\gamma_{2,S}$ represents the activity coefficient of E-1-chloro-3,3,3-trifluoro-1-propene (1233zdE) in said organic extracting agent at infinite dilution;
- P2 represents the saturating vapor pressure of E-1-chloro-3,3,3-trifluoro-1-propene (1233zdE);
- advantageously, the separation factor $S_{1,2}$ is greater than or equal to 1.2, preferably greater than or equal to 1.4, more preferentially greater than or equal to 1.6, in particular greater than or equal to 1.8, more particularly greater than or equal to 2.0;

and said organic extracting agent may have an absorption capacity $C_{2,S}$ of greater than or equal to 0.20, said absorption capacity being calculated by the formula $C_{2,S} = 1/(\gamma_{2,S})$ in which $\gamma_{2,S}$ represents the activity coefficient of E-1-chloro-3,3,3-trifluoro-1-propene (1233zdE) in said organic extracting agent at infinite dilution; advantageously, the absorption capacity $C_{2,S}$ is greater than or equal to 0.40, preferably greater than or equal to 0.60, more preferentially greater than or equal to 0.8, in particular greater than or equal to 1.0.

Thus, in a particular embodiment, said organic extracting agent may be chosen from the group consisting of isopropylmethylamine, methyl t-butyl ether, diethylamine, propanone, methyl acetate, 2-butanamine, n-methylpropylamine, tetrahydrofuran, 1-butylamine, ethyl acetate, butanone, n-propyl formate, -dimethoxypropane, diisopropylamine, 1,2-dimethoxyethane, 3-methyl-2-butanamine, diethoxymethane, isopropyl acetate, 3-pentylamine, n-methylbutylamine, 1-methoxy-2-propanamine, 2-methoxyethanamine, tert-butyl acetate, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 1,2-diaminoethane, 1-methoxy-2-propanol, 1,2-propanediamine, 2,6-dimethyl-5-heptenal, 1-(dimethylamino)-2-propanol, 3-methyl-3-pentanol, 2-ethylbutylamine, diethyl carbonate, n-butyl acetate, 2-hexanone, n-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-ethoxy-1-propanol, 1-methylpiperazine, 1,3-propanediamine, 2-heptanamine, n,n-diethylethylenediamine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol, 1-propoxy-2-propanol, 2-heptanone, dimethylformamide, 2-isopropoxyethanol, 2-methylpiperazine, cyclohexanone, 1-heptanamine, 2-ethoxyethyl acetate, 1,4-butanediamine, 2,4-dimethylpyridine, 2-methoxy-3-methylpyrazine, 4-methoxy-4-methylpentan-2-one, 3-ethoxy-1-propanol, 3-methoxy-1-butanol, diglyme, 2-(diethylamino)ethanol, 2,2-diethoxyethanamine, 2-methoxy-n-(2-methoxyethyl)ethanamine, 2-(ethylamino)ethanol, 3-octanone, diacetone alcohol, diethylaminopropylamine, 2-ethylhexylamine, 1-butoxy-2-propanol, 2-butoxyethanol, 2-octanone, methyl heptanoate, triethylenediamine, n,n-dimethylpropanamide, 2-propyl 1-methoxypropanoate, 1,5-pentanediamine, cycloheptanone, 3,4-dimethylpyridine, 1-octanamine, benzylmethanamine, 1,1,3,3-tetramethoxypropane, dihexyl phthalate, diethylpropanolamine, 2-butoxyethyl acetate, diethyl sulfoxide, 2-(2-methoxyethoxy)ethanol, 4-methylbenzenemethanamine, diethylene glycol monoethyl ether, 2-propylcyclohexanone, trimethyl phosphate, 2-methyl-2,4-pentanediol, methyl benzoate, diethyl malonate and 2-methoxypyrimidine; preferably, said organic extracting agent is chosen from the group consisting of diethylamine, propanone, methyl acetate, tetrahydrofuran, ethyl acetate, butanone, diethoxymethane, isopropyl acetate, tert-butyl acetate, dioxane, 3-pentanone, 1,1-diethoxyethane, 2-pentanone, n-pentylamine, 1,3-dioxane, sec-butyl acetate, 1,2-diaminoethane, 1-methoxy-2-propanol, n-butyl acetate and 1-ethoxy-2-propanol. Preferably, this particular embodiment may allow efficient separation of 2-chloro-3,3,3-trifluoropropene and E-1-chloro-3,3,3-trifluoro-1-propene (1233zdE).

According to a preferred embodiment, to promote the simultaneous removal of E-1-chloro-3,3,3-trifluoro-1-propene (1233zdE) and 1,1,1,3,3-pentafluoropropane (245fa), said organic extract agent placed in contact with the stream L1d may be chosen from the group consisting of propanone, methyl acetate, ethyl acetate, butanone, dioxane, trimethoxymethane, 1,3-dioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, n,n-dimethylpropanamide, diethyl sulfoxide, 2-(2-methoxyethoxy)ethanol, trimethyl phosphate and diethyl malonate. In particular, said organic extracting agent may be chosen from the group consisting of propanone, methyl acetate, ethyl acetate, butanone, dioxane, trimethoxymethane, 1,3-dioxane, 1,2-diaminoethane, 1-methoxy-2-propanol, 3-methoxy-1-butanol and diacetone alcohol.

According to a preferred embodiment, said stream L1g comprising E-1-chloro-3,3,3-trifluoro-1-propene (1233zdE), 1,1,1,3,3-pentafluoropropane (245fa) and said organic extracting agent may be distilled to separate, on the one hand, said organic extracting agent and, on the other hand, E-1-chloro-3,3,3-trifluoro-1-propene (1233zdE) and 1,1,1,3,3-pentafluoropropane (245fa). Preferably, said organic extracting agent may be recycled.

According to a preferred embodiment, the stream L1f comprising 2-chloro-3,3,3-trifluoro-1-propene (1233xf) is recycled into step a).

If heavy impurities are present in said stream L1d, it may be distilled prior to its separation to remove said impurities. The stream L1d as described above may be recovered at the top of the distillation column, the heavy impurities being recovered at the bottom of the distillation column. The heavy impurities may contain, for example, 1,2-dichloro-3,3,3-trifluoropropene (1223xd), dimers or trimers derived from one of the compounds present in the composition or the stream under consideration.

More particularly, the starting composition may comprise 1,1,2,3-tetrachloropropene, 2,3,3,3,-tetrachloropropene, 1,1,3,3-tetrachloropropene, 1,3,3,3-tetrachloropropene, 1,1,1,2,3-pentachloropropane, 1,1,1,3,3-pentachloropropane, 1,1,2, 2,3-pentachloropropane, 1,2-dichloro-3,3,3-trifluoropropane, 2-chloro-2,3,3,3-tetrafluoropropane, 1,1,1,2,2-pentafluoropropane, 1-chloro-1,3,3,3-tetrafluoropropane and 1,1,1,3,3-pentafluoropropane, preferably 1,1,1,2,3-pentachloropropane, 1,1,2,3,tetrachloropropene, 1,1,1,2,2-pentafluoropropane and/or 2-chloro-3,3,3-trifluoro-1-propene; in particular 1,1,1,2,3-pentachloropropane (240db).

The catalyst used in the present process for producing 2,3,3,3-tetrafluoropropene may be based, for example, on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments) and chromium fluorides, and mixtures thereof. Other possible catalysts are catalysts supported on carbon, antimony-based catalysts, and aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or an optionally supported catalyst containing a metal such as Cr, Ni, Fe, Zn, Ti, V, Zr, Mo, Ge, Sn, Pb, Mg or Sb.

Reference may be made in this respect to WO 2007/079431 (on page 7, lines 1-5 and 28-32) and EP 939071 (paragraph [0022]), WO 2008/054781 (on page 9, line 22 to page 10, line 34) and WO 2008/040969 (claim 1), to which reference is expressly made.

The catalyst is more particularly preferably chromium-based and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5% to 20% by weight of nickel.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support which has optionally been subjected to activation.

Reference may be made to WO 2009/118628 (especially on page 4, line 30 to page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF.

For example, the catalyst is preferably subjected to activation with air or oxygen and HF at a temperature from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, HF and organic compounds.

The HF/organic compounds mole ratio is preferably from 2 to 40 and the oxidizing agent/organic compounds mole ratio is preferably from 0.04 to 25. The temperature of the final activation is preferably from 300 to 400° C. and its duration is preferably from 6 to 100 hours.

The gas-phase fluorination reaction may be performed:
with an HF/compound of formula (I) and/or (II) mole ratio from 3:1 to 150:1, preferably from 4:1 to 125:1 and more particularly preferably from 5:1 to 100:1;
with a contact time from 3 to 100 seconds, preferably 4 to 75 seconds and more particularly 5 to 50 seconds (volume of catalyst divided by the total entering stream, adjusted to the operating temperature and pressure);
at a pressure ranging from atmospheric pressure to 20 bar, preferably from 2 to 18 bar and more particularly from 3 to 15 bar;
at a temperature (temperature of the catalytic bed) from 200 to 450° C., preferably from 250 to 400° C. and more particularly from 280 to 380° C.

The duration of the reaction step is typically from 10 to 8000 hours, preferably from 50 to 5000 hours and more particularly preferably from 70 to 1000 hours.

An oxidizing agent, preferably oxygen, may optionally be added during the fluorination reaction. The oxygen/organic compounds mole ratio may be from 0.005 to 2, preferably from 0.01 to 1.5. Oxygen may be introduced in pure form or in the form of air or an oxygen/nitrogen mixture. Oxygen may also be replaced with chlorine.

FIG. 1 schematically illustrates a device for performing a process for producing 2,3,3,3-tetrafluoropropene according to a particular embodiment of the present invention. Hydrofluoric acid 1 is placed in contact with 1,1,1,2,3-pentachloropropane (240db) 2 in one or more reactors 3. The mixture obtained, comprising 2,3,3,3-tetrafluoro-1-propene, 1,1,1,2,2-pentafluoropropane (245cb), trans-1,3,3,3-tetrafluoro-1-propene (1234zeE), 2-chloro-3,3,3-trifluoropropene (1233xf), E-1-chloro-3,3,3-trifluoro-1-propene (1233zdE) and 1,1,1,3,3-pentafluoropropane (245fa), is recovered at the reactor outlet and conveyed to a distillation column 5 via pipe 4. The mixture may also comprise HCl, unreacted HF and heavy impurities or impurities with a boiling point below that of 2,3,3,3-tetrafluoro-1-propene. All or some of the stream obtained at the bottom of the distillation column is conveyed to the purification device 13 via pipe 7. HF, 2-chloro-3,3,3-trifluoropropene (1233xf) and 1,1,1,2,2-pentafluoropropane (245cb) and optionally trans-1,3,3,3-tetrafluoro-1-propene (1234zeE) may be extracted from this purification device 13, which are recycled into the reactor 3 via pipe 15. E-1-chloro-3,3,3-trifluoro-1-propene (1233zdE) and 1,1,1,3,3-pentafluoropropane (245fa) may also be extracted from the device 13 to be evacuated in 14 to an incinerator or a purification device. A stream is also recovered at the top of the distillation column 5 and conveyed to a purification device 7 via pipe 6. From the purification device 7, a stream comprising 2,3,3,3-tetrafluoro-1-propene is recovered in 11 via pipe 8. A stream comprising 1,1,1,2,2-pentafluoropropane (245cb), and optionally trans-1,3,3,3-tetrafluoro-1-propene (1234zeE) is also obtained and recycled into reactor 3 via pipe 10. Finally, a stream comprising trans-1,3,3,3-tetrafluoro-1-propene (1234zeE) may be recovered at 12 via pipe 9.

Figure 2:
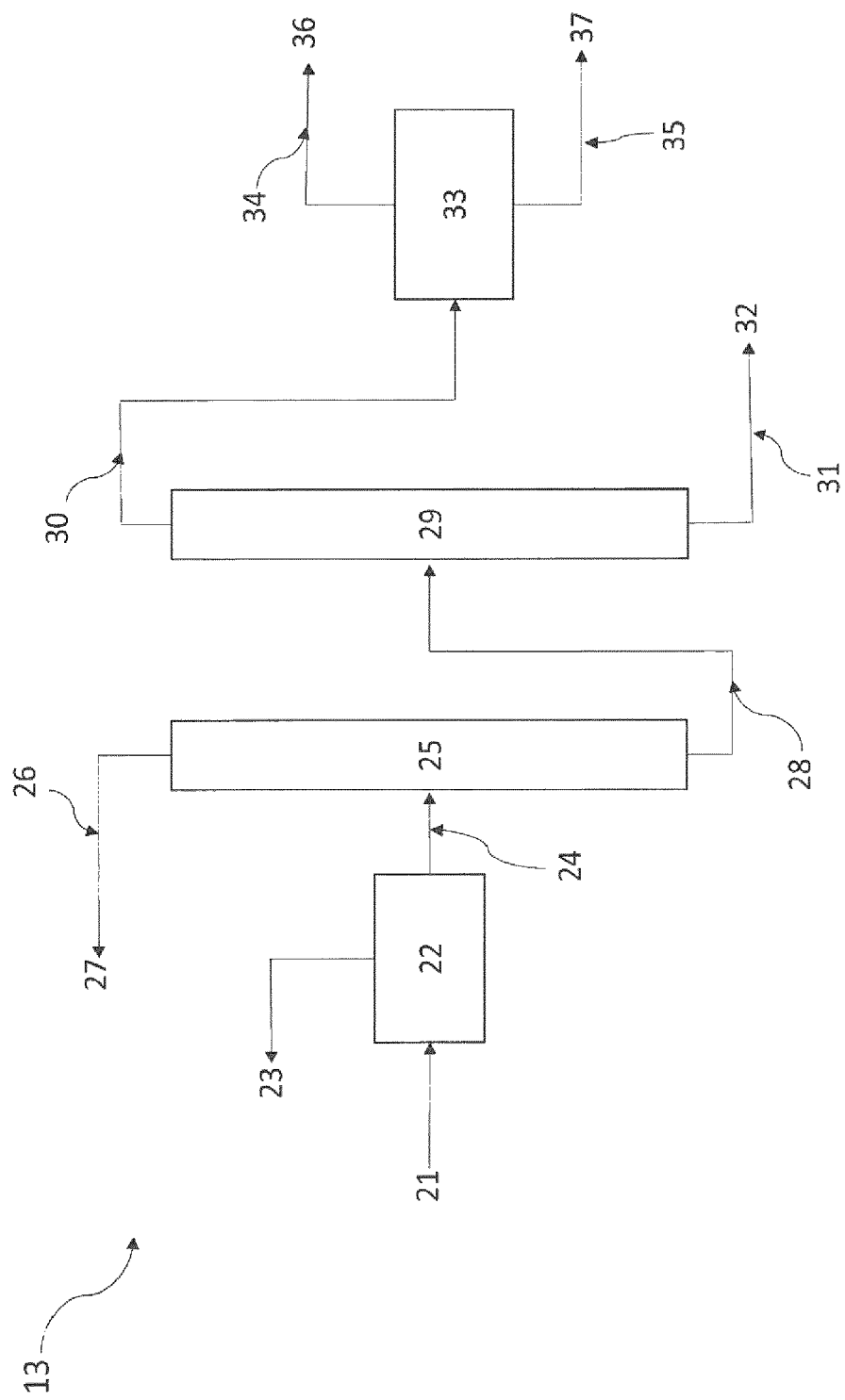
FIGS. 2 and 3 schematically represent a device for performing the purification of 2-3,3,3-tetrafluoro-1-propene according to a particular embodiment of the present invention.

FIG. 2 schematically illustrates, according to a particular embodiment of the present invention, a purification device 13. A stream 21 especially comprising HF, trans-1,3,3,3-tetrafluoro-1-propene (1234zeE), 1,1,1,2,2-pentafluoropropane (245cb), 2-chloro-3,3,3-trifluoropropene (1233xf), E-1-chloro-3,3,3-trifluoro-1-propene (1233zdE) and 1,1,1,3,3-pentafluoropropane (245fa) is conveyed to the decanter 22 with a temperature of −25° C. HF is extracted and recovered at 23 to be recycled into reactor 3. The other constituents are conveyed to the distillation column 25 via pipe 24. The trans-1,3,3,3-tetrafluoro-1-propene (1234zeE) and 1,1,1,2,2-pentafluoropropane (245cb) are removed from the top of the distillation column and recovered at 27 via pipe 26. They may be recovered to be recycled into reactor 3. The 2-chloro-3,3,3-trifluoropropene (1233xf), E-1-chloro-3,3,3-trifluoro-1-propene (1233zdE) and 1,1,1,3,3-pentafluoropropane (245fa) are conveyed to the distillation column 29 via pipe 28 to extract, at the bottom of the distillation column, any heavy impurities present and to convey them to an incinerator 32 via pipe 31. The 2-chloro-3,3,3-trifluoropropene (1233xf), E-1-chloro-3,3,3-trifluoro-1-propene (1233zdE) and 1,1,1,3,3-pentafluoropropane (245fa) recovered at the top of the distillation column 29 are conveyed to a purification device 33 via pipe 30. From this purification device 33, 2-chloro-3,3,3-trifluoropropene (1233xf) may be extracted at 36 via pipe 34. The purification device 33 may be extractive distillation. The E-1-chloro-3,3,3-trifluoro-1-propene (1233zdE) and 1,1,1,3,3-pentafluoropropane (245fa) may be recovered at 37 via pipe 35 to be incinerated or purified.

Figure 3:
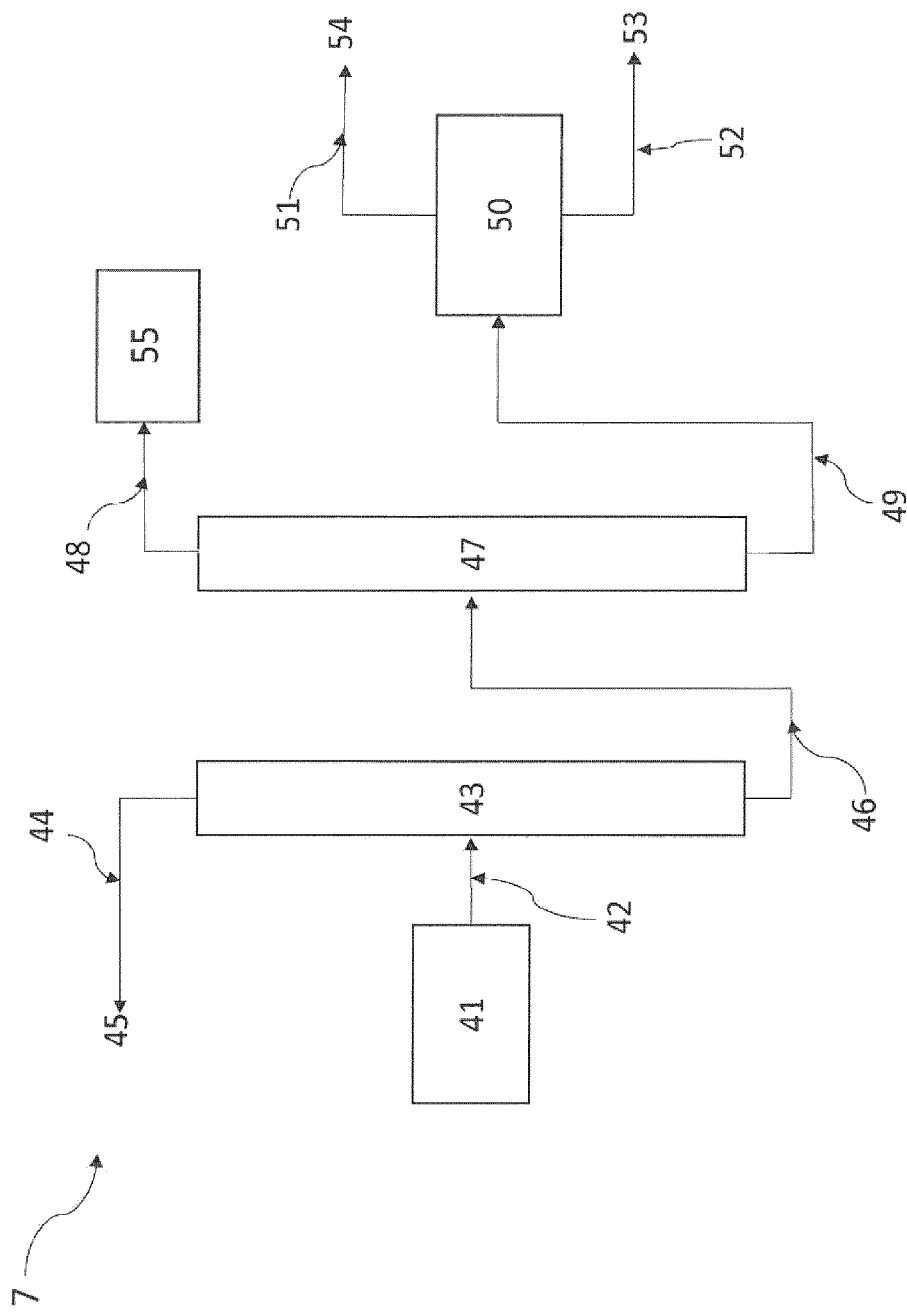

FIG. 3 schematically illustrates, according to a particular embodiment of the present invention, a purification device 7. A storage tank 41 comprises 2,3,3,3-tetrafluoro-1-propene, trans-1,3,3,3-tetrafluoro-1-propene (1234zeE), 1,1,1,1,2,2-pentafluoropropane (245cb) and impurities with a boiling point below that of 2,3,3,3-tetrafluoro-1-propene. This mixture is conveyed to the distillation column 43 via pipe 42. The impurities with a boiling point below that of 2,3,3,3-tetrafluoro-1-propene are removed at 45 via pipe 44. The other constituents of the mixture are conveyed to the distillation column 47 via pipe 46. A stream comprising 2,3,3,3-tetrafluoro-1-propene is recovered at the top of the distillation column and removed at 48 to storage tanks or an additional purification device 55, for example an extractive distillation device. The trans-1,3,3,3-tetrafluoro-1-propene (1234zeE) and 1,1,1,2,2-pentafluoropropane (245cb) are recovered at the bottom of the distillation column and conveyed to a purification device 50 via pipe 49. A stream comprising 1,1,1,2,2-pentafluoropropane (245cb) separated from the trans-1,3,3,3-tetrafluoro-1-propene (1234zeE) is recovered at 53 via pipe 52. The stream comprising 1,1,1,2,2-pentafluoropropane (245cb) recovered at 53 may be recycled into reactor 3. A stream comprising trans-1,3,3,3-tetrafluoro-1-propene (1234zeE) is recovered at 54 via pipe 51 to be incinerated or purified. The purification device 50 may be extractive distillation.

The invention claimed is:

1. A process for producing and purifying 2,3,3,3-tetrafluoropropene (1234yf) which is performed using a starting composition comprising 1,1,2,3-tetrachloropropene, 2,3,3,3,-tetrachloropropene, 1,1,3,3-tetrachloropropene, 1,3,3,3-tetrachloropropene, 1,1,1,2,3-pentachloropropane, 1,1,1,3,3-pentachloropropane, 1,1,2,2,3-pentachloropropane, 1,2-dichloro-3,3,3-trifluoropropane, 2-chloro-2,3,3,3-tetrafluoropropane, 1,1,1,2,2-pentafluoropropane, 1-chloro-1,3,3,3-tetrafluoropropane or 1,1,1,3,3-pentafluoropropane; said process comprising:
 a) placing the starting composition in contact, in the presence of a catalyst, with HF to produce a composition A comprising HCl, part of the unreacted HF, 2,3,3,3-tetrafluoropropene (1234yf), intermediate products B comprising 2-chloro-3,3,3-trifluoropropene (1233xf), 1,1,1,2,2-pentafluoropropane (245cb), and side products C comprising E-1-chloro-3,3,3-trifluoro-1-propene (1233zdE), trans-1,3,3,3-tetrafluoro-1-propene (1234zeE) and 1,1,1,3,3-pentafluoropropane (245fa);
 b) recovering and purifying said composition A to form and recover a first stream comprising HCl, 2,3,3,3-tetrafluoropropene (1234yf), part of the intermediate products B and part of the side products C; and a stream L1 comprising part of the unreacted HF, part of the intermediate products B and part of the side products C;
 c) purifying said first stream to form a stream comprising a portion of said part of the intermediate products B and a portion of said part of the side products C and recycling thereof into step a);
 d) bringing all or part of the liquid stream L1 to a low temperature, between −50° C. and 20° C., to form a first phase L1a comprising part of the unreacted HF; and
 e) recycling said first phase L1a into step a).

2. The process as claimed in claim 1, wherein said first stream purified in step c) is a gaseous stream G1, which is purified using the following steps:
 b1) distilling the gaseous stream G1 to recover a stream G1a comprising HCl, at the top of the distillation column, and a stream G1b comprising 2,3,3,3-tetrafluoropropene (1234yf), said part of the intermediate products B and said part of the side products C, at the bottom of the distillation column;
 b2) distilling said stream G1b obtained in step b1) to form a stream G1c comprising 2,3,3,3-tetrafluoropropene (1234yf), a portion of said part of the intermediate products B and a portion of said part of the side products C, at the top of the distillation column, and a stream G1d comprising a portion of said part of the intermediate products B and a portion of said part of the side products C, at the bottom of the distillation column.

3. The process as claimed in claim 2, wherein the stream G1c is distilled according to the following steps:
 b4') placing said stream G1c obtained in step b2) in contact with an organic extracting agent to form a stream G1g', and
 b5') distilling stream G1g' by extractive distillation to form the stream G1e' comprising 2,3,3,3-tetrafluoropropene (1234yf) and 1,1,1,2,2-pentafluoropropane (245cb), at the top of the distillation column, and the stream G1h' comprising trans-1,3,3,3-tetrafluoro-1-propene (1234zeE) and said organic extracting agent, at the bottom of the distillation column.

4. The process as claimed in claim 2, wherein when said liquid stream L1 is brought to low temperature, between −50° C. and 20° C., to form a first phase L1a comprising part of the unreacted HF, additionally a second phase L1b comprising said intermediate products B and said side products C is formed; optionally, said stream G1d formed in step b2) is mixed with the liquid stream L1 before said stream is brought to low temperature.

5. The process as claimed in claim 4, further comprising distilling said second phase L1b to recover a stream L1c comprising 1,1,1,2,2-pentafluoropropane (245cb) and trans-1,3,3,3-tetrafluoro-1-propene (1234zeE), at the top of the distillation column, and a stream L1d comprising 2-chloro-3,3,3-trifluoro-1-propene (1233xf), E-1-chloro-3,3,3-trifluoro-1-propene (1233zdE) and 1,1,1,3,3-pentafluoropropane (245fa), at the bottom of the distillation column; and recycling said stream L1c into step a).

6. The process as claimed in claim 5, wherein said stream L1d is separated out to form a stream comprising 2-chloro-3,3,3-trifluoro-1-propene (1233xf) and a stream comprising E-1-chloro-3,3,3-trifluoro-1-propene (1233zdE) and 1,1,1,3,3-pentafluoropropane (245fa).

7. The process as claimed in claim 6, wherein the separation of said stream L1d is performed by extractive distillation.

8. The process as claimed in claim 7, wherein the extractive distillation of said stream L1d comprises:
   placing said stream L1d in contact with an organic extracting agent to form a composition L1e, and
   distilling composition L1e by extractive distillation to form a stream L1f comprising 2-chloro-3,3,3-trifluoro-1-propene (1233xf), at the top of the distillation column, and a stream L1g comprising E-1-chloro-3,3,3-trifluoro-1-propene (1233zdE) and 1,1,1,3,3-pentafluoropropane (245fa) and said organic extracting agent, at the bottom of the distillation column.

9. The process as claimed in claim 7, wherein the stream L1f comprising 2-chloro-3,3,3-trifluoro-1-propene (1233xf) is recycled into step a).

10. The process as claimed in claim 8, wherein the starting composition comprises 1,1,1,2,3-pentachloropropane, 1,1,2,3,tetrachloropropene, 1,1,1,2,2-pentafluoropropane or 2-chloro-3,3,3-trifluoro-1-propene.

* * * * *